US005738855A

United States Patent [19]

Szu et al.

[11] Patent Number: 5,738,855

[45] Date of Patent: Apr. 14, 1998

[54] SYNTHESIS OF TYPHOID FEVER VACCINE FROM A PLANT OR FRUIT POLYSACCHARIDE

[75] Inventors: Shousun Chen Szu, Bethesda; Slavomir Bystricky, Silver Springs, both of Md.

[73] Assignee: The United States of America as represented by the Secretary of the Department of Health and Human Services, Washington, D.C.

[21] Appl. No.: 323,918

[22] Filed: Oct. 17, 1994

[51] Int. Cl.[6] .......................... A61K 39/00; A61K 39/385; A61K 45/00; C07G 17/00

[52] U.S. Cl. .......................... 424/258.1; 424/184.1; 424/197.1; 424/236.1; 424/192.1; 536/123; 514/2; 514/53; 530/402

[58] Field of Search .......................... 536/123; 424/197.11, 424/184.1, 192.1, 236.1, 258.1, 253; 514/253; 530/402

[56] References Cited

U.S. PATENT DOCUMENTS 5,204,098 4/1993 Szu et al. .......................... 424/92

OTHER PUBLICATIONS

Stone et al. 1988. J. Clin. Microbiol. 26(4):719–25.

Potievskii et al. 1994 Zhurnal Mikrobiologii Epidemiologii Immunobiologii 106–109.

Merck Index 183 $10^{th}$ Edition, p. 6922.

Fattom et al. 1988 Infect & Immunity. 56(9):2292–98.

Robbins et al. J. Infectious Dis. 1990 161:821–832.

Szu et al, Synthesis and Some Immunologic Properties of an O–Acetyl Pectin [Poly(1→4)–α–D–GalpA]–Protein Conjugate as a Vaccine for Typhoid Fever, *Infection and Immunity*, Dec. 1994, pp. 5545–5549, vol. 62, No. 12.

Acharya et al, Prevention of Typhoid Fever in Nepal with the Vi Capsular Polysaccharide of *Salmonella typhi*, *New England Journal of Medicine*, 317:1101–1105, Oct. 29, 1987.

Devi et al, Antibodies to Poly[2→8)–α–N–Acetylneuraminic Acid] and Poly[(2→9)–α–N–Acetylneuraminic Acid] Are Elicited by Immunication of Mice with *Escherichia coli* K92 Conjugates: Potential Vacines for Groups B and C Meningococci and *E. coli* K1, *Proc. Natl. Acad. Sci.* vol. 88, pp. 7175–7179, Aug. 1991.

Klugman et al, Protective Activity of V1 Capsular Polysaccharide Vaccine Against Typhoid Fever, *The Lancet*, Nov. 21, 1987, pp. 1165–1169.

Landy et al, Studies On Vi Antigen VIII. Role of Acetyl in Antigenic Activity, *Am. J. Hvg.*, 1961, vol. 73, pp. 55–65.

Whiteside et al, The Vi Antigens of the Enterobacteriaceae V. Serologic Differences of V1 Antigens Revealed by Deacetylation, *J. Immunol.*, Sep. 21, 1961, vol. 86, pp. 538–542.

Szewczyk et al, Immunochemical Properties of Vi Antigen From *Salmonella typhi* TY2: Presence of Two Antigenic Determinants, *Infection and Immunity*, Aug. 1980, pp. 539–544, vol. 29, No. 2.

Szu et al, Vi Capsular Polysaccharide–Protein Conjugates for Prevention of Typhoid Fever, *Journal of Experimental Medicine*, vol. 166, Nov. 1987, pp. 1510–1524.

Szu et al, Laboratory and Preliminary Clinical Characterization of Vi Capsular Polysaccharide–Protein Conjugate Vaccines, *Infection and Immunity*, vol. 62 (Oct.), pp. 4440–4444, 1994.

Robbins, J.D. et al, Re–Examination of Protective Role of the Vi Capsular Polysaccharide (Vi Antigen) of *Salmonella typhi*, *J. Infect. Disease*, vol. 150 (No. 3), pp. 436–499, 1984.

*Primary Examiner*—N. M. Minnifield
*Attorney, Agent, or Firm*—Morgan & Finnegan, L.L.P.

[57] ABSTRACT

The present invention is a modified plant, fruit or synthetic oligo- or polysaccharide which has been structurally altered so as to render the modified saccharide antigenically similar to the Vi of *Salmonella typhi*. The modified saccharide may be conjugated to a carrier to form a conjugate that is immunogenic against *S. typhi*. Antibodies produced in response to the immunogenic conjugate are protective against typhoid fever. Methods are provided for making the modified saccharide and the immunogenic conjugate.

49 Claims, 4 Drawing Sheets

SYNTHESIS OF TYPHOID FEVER VACCINE FROM A PLANT OR FRUIT POLYSACCHARIDE

FIELD OF THE INVENTION

The present invention relates to immunoprophylaxis and vaccines. More particularly it relates to modifying a plant, fruit or synthetic polysaccharide such that it is immunogenic and may be used as a vaccine to prevent typhoid fever in infants and young children.

BACKGROUND OF THE INVENTION

Typhoid fever, caused by *Salmonella typhi*, remains a common and serious disease in many parts of the world. The capsular polysaccharide (Vi) is both an essential virulence factor and a protective antigen of *Salmonella typhi* [19]. Tacket et al. in *J. Infect. Dis.* 154:342–345 (1986) disclose a vaccine made from the Vi capsular polysaccharide of *Salmonella typhi*. Field trials in Nepal and in the Republic of South Africa showed that a single injection of Vi conferred about 70% protection against typhoid fever in older children and in adults [1,13]. The mechanism of its protective action, similar to other polysaccharide vaccines, is to elicit a critical level of serum antibodies.

The immunologic properties of the Vi that limits its use as a vaccine are: 1) only ~70% efficacy in individuals 5 to 45 years of age; 2) an age-dependent serum antibody response, Vi elicited a comparatively short-lived antibody responses in 2 to 5 year old children and only low levels of antibodies in a fraction of children <2 years-old and; 3) reinjection did not elicit a booster antibody response (T-cell independent) [15, 19]. To increase its immunogenicity and to induce T-cell dependence, the Vi was conjugated to proteins [22,24,25]. A clinical trial in adults in the United States showed that Vi-protein conjugates elicited significantly higher levels of serum antibodies than the Vi alone [25].

The Vi is a linear homopolymer of (1→4)-α-D-GalApNAc, variably O-acetylated at $C_3$ (FIG. 1) [19, 23]. Whiteside and Baker in *J. Immunol.* 86:538–542 (1961) and Landy et al., *Am. J. Hyg.* 73:55–65 (1961) disclose that the O-acetyl groups on Vi is essential for its antigenicity. Szu et al. disclose a conjugate scheme for Vi capsular polysaccharide covalent bound to a carrier protein (22, 23, 24). However, synthesis of Vi-protein conjugates poses several problems. First, the high molecular weight of Vi (~$2\times10^3$ kD) causes conjugates to be poorly soluble. Second, standardization of Vi conjugates has been hindered by a lack of a colorimetric method for quantification of this polysaccharide [21]. Colorimetric methods are not applicable to the Vi because the polyhexosaminuronic acid structure resists acid hydrolysis and does not form a chromophore in the carbazole assay.

Szewczyk and Taylor in *Infect. Immun.* 29:539–544 (1980) taught the art of O-acetylated polygalacturonic acid to form a compound that is antigenically indistinguishable from the Vi as determined by immunodiffusion. The O-acetylated pectin, even though antigenic, is not immunogenic in vivo. Avery and Goebel in *J. Exp. Med.* 50:531 (1929) and Goebel in *J. Exp. Med.* 50:469–520 (1929) showed that the immunogenicity of pneumococcus type 3 polysaccharide could be increased by binding it chemically to a carrier protein. This principle has been applied successfully to increase the immunogenicity of capsular polysaccharides of other pathogens (7, 10, 22, 24).

Until the present invention, the art has not shown a plant or fruit derived O-acetylated oligo- or polygalacturonate that is both antigenic and innnunogenic against *S. typhi.*

SUMMARY OF THE INVENTION

It is an object of the present invention to overcome deficiencies in the prior art, such as those noted above.

It is a further object of the present invention to produce an antigen based on a plant, fruit or synthetic oligo- or polysaccharide which is immunologically similar to the Vi antigen of *Salmonella typhi*. Preferably the oligo- or polysaccharide is based on pectin which has been modified by acetylation at the $C_2$ and/or $C_3$ hydroxyls of its galacturonate subunit.

It is yet another object of the present invention to provide an immunogen that elicites antibodies that bind Vi of *S. typhi* in which the immunogen is based on a plant, fruit or synthetic oligo- or polysaccharide conjugated with a carrier.

It is yet another object of the present invention to provide antibodies against Vi of *S. typhi* which are elicited by immunization with a plant, fruit or synthetic polysaccharide-carrier conjugate.

According to the present invention, methods are provided to synthesize a modified plant, fruit or synthetic oligo- or polysaccharide which is structurally similar to the Vi antigen.

According to the present invention, methods are provided to conjugate the modified plant, fruit or synthetic oligo- or polysaccharide with a carrier.

DETAILED DESCRIPTION OF THE INVENTION

Figure 1:
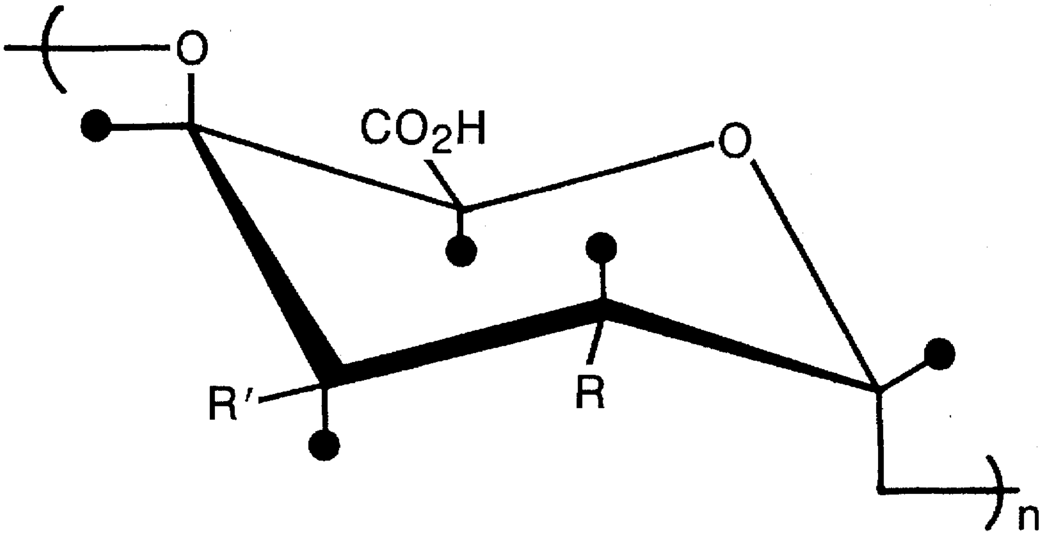
FIG. 1 shows the structure of the repeating unit of the Vi, the pectin and the O-acetylated pectin. For Vi, $C_2$ (R) is N-acetylated and $C_3$ ($R^1$) is O-acetylated; for pectin, $C_2$ and $C_3$ are hydroxylated; for OAcPec, $C_2$ and $C_3$ are O-acetylated, n=number of subunits.

The Vi molecule of *Salmonella typhi* has a simple structure which is a linear polysaccharide having repeating sugar subunits. The antigenicity and immunogenicity of Vi depends on its N- acetyl at $C_2$ and O-acetyl at $C_3$ on each galacturonate subunit [19,23]. As shown for Vi and other polysaccharides, removal of the O-acetyls removed most of the antigenicity and all of the immunogenicity of the Vi [23,26]. The precise role of N-acetyl is not known as selective removal of the N-acetyl on Vi has not been accomplished. The present invention mimics the simple structure of Vi by modification of plant, fruit or synthetic saccharides. The modified plant, fruit or synthetic saccharides resemble Vi in antigenic and immunogenic properties and as such they have the capacity to act as an effective vaccines against typhoid fever.

The present invention encompasses a modified plant, fruit or synthetic oligosaccharide or polysaccharide. Oligosaccharide as defined herein is a carbohydrate containing from two to ten simple sugar subunits linked together. A polysaccharide as defined herein is a carbohydrate containing more than ten simple sugar subunits linked together. The present invention preferably encompasses a modified pectin or modified D-galacturonan, oligogalacturonate or polygalacturonate and mixtures thereof. As used herein, modified pectin or modified oligogalactunonate or polygalacturonate refers to native or naturally occurring pectin or synthetic D-galacturonan, oligogalacturonate and polygalacturonate that has been structurally altered. Such structural alterations are any alterations that render the modified pectin or modified D-galacturonan, oligogalacturonate or polygalacturonate antigenically similar to the Vi antigen of *Salmonella typhi*. The structural alterations substantially approximate the structure of the Vi antigen of *S. typhi*.

Preferably, a modified pectin, D-galacturonan, oligo-, and polygalacturonate of this invention is further characterized by its ability to immunologically mimic an epitope (antigenic determinant) expressed by *S. typhi*. Such a modified pectin, D-galacturonan, oligo-, and polygalacturonate is useful herein as a component in an inoculum for producing antibodies that immunoreact with *S. typhi*, and preferably immunoreact with the Vi of *S. typhi*.

As used herein, the phrase "immunologically mimic" in its various grammatical forms refers to the ability of a modified pectin, modified D-galacturonan, oligogalacturonate and polygalacturonate of this invention to immunoreact with an antibody of the present invention that recognizes and binds to a native epitope on the Vi of *S. typhi* as defined herein.

It should be understood that a subject modified pectin, modified D-galacturonan, oligogalacturonate and polygalacturonate need not be structurally identical to the Vi antigen so long as it includes the required sterical structure and is able to elicit antibodies that react with the Vi antigen on *S. typhi*.

A subject modified pectin, modified D-galacturonan, oligogalacturonate and polygalacturonate includes any substituted analog, fragment or chemical derivative of a pectin so long as the modified pectin, modified D-galacturonan, oligogalacturonate and polygalacturonate is capable of reacting with antibodies that react with the Vi antigen. Therefore, a present modified pectin, modified D-galacturonan, oligogalacturonate and polygalacturonate can be subject to various changes that provide for certain advantages in its use.

The phrase "substitution" includes the use of a chemically derivatized residue in place of a non-derivatized residue provided that such modified pectin, modified D-galacturonan, oligogalacturonate and polygalacturonate display the requisite immunological activity.

"Chemical derivative" refers to a subject modified pectin, modified D-galacturonan, oligogalacturonate and polygalacturonate having one or more residues chemically derivatized by reaction of a functional side group. Additional residues may also be added for the purpose of providing a "linker" by which the modified pectin, modified D-galacturonan, oligogalacturonate and polygalacturonate of this invention can be conveniently affixed to a label or solid matrix or carrier. Labels, solid matrices and carriers that can be used with the polypeptides of this invention are described herein below.

The present invention encompasses a modified pectin, modified D-galacturonan, oligogalacturonate and polygalacturonate in which the monosaccharide subunit(s) have one O-acetylated carbon, preferably two O-acetylated carbons. In one embodiment, at least $C_3$ or $C_2$ is O-acetylated. In another embodiment, $C_3$ and $C_2$ are O-acetylated. In a preferred embodiment, at least 50% of $C_2$ and $C_3$ are O-acetylated.

The Vi molecule has N-acetyl groups at position $C_2$ and O-acetyl groups at position $C_3$. If all of the $C_2$ positions have acetyl groups and all the $C_3$ positions on Vi contain acetyl groups, then by definition, the Vi molecule is theoretically 200% fully acetylated. In most preparations of Vi the percent acetylation varies. The $C_2$ position is usually about 100% N-acetylated and the $C_3$ position is from about 60–90% O-acetylated depending on normal variation in preparations of Vi. The modified pectin, D-galacturonan, oligogalacturonate and polygalacturonate of the present invention approximates the total percent acetylation of Vi.

The modified pectin, D-galacturonan, oligogalacturonate and polygalacturate of the present invention are from about 50% to about 200% O-acetylated, preferably from about 80% to about 200% O-acetylated, more preferably from about 160% to about 190% O-acetylated.

In one embodiment, the modified pectin and the modified D-galacturonan, oligogalacturonate and polygalacturate of the present invention has a molar ratio of O-acetyl groups/mole galacturonan sufficient to elicit antibodies that bind to Vi. The molar ratio may be at least 0.5 mole of O-acetyl/mole galacturonan (Gal A), preferably at least 1.6 moles O-acetyl/mole Gal A, more preferably between about 1.6 and about 1.9 moles O-acetyl/mole Gal A. In one embodiment, the ratio is about 1.9 moles O-acetyl/mole Gal A.

Lower molar ratios may be used for the present invention if the O-acetylated pectin, D-galacturonan, oligogalacturonate and polygalacturanate is shown to be immunogenic by screening techniques described herein.

As with other polysaccharides, the molecular weight of the Vi alone and as a Vi-carrier conjugate is related to its immunogenicity [16, 17, 22]. Thus, the modified pectin and modified D-galacturonan, oligogalacturonate and polygalacturonate may vary in molecular weight in order to enhance its antigenicity or to enhance its immunogenicity when in a conjugate form. The modified pectin and modified D-galacturonan, oligogalacturonate and polygalacturonate may have from about 2 to about 1,000 modified galacturonic subunits, preferably from about 50 to about 800, more preferably from about 200 to about 600 monosaccharide subunits. The molecular weight of the modified pectin may range from about 100 to about 1,000,000, preferably from about 200,000 to about 600,000. In one embodiment the molecular weight of the modified pectin is approximately 400 kD.

In addition to the modifications of the galacturonic acid at position $C_2$ or $C_3$, other substitutions or deletions are encompassed, such that the substitutions or deletions result in a modified pectin and modified D-galacturonan, oligogalacturonate and polygalacturonate that is antigenically similar to the Vi antigen of *S. typhi*.

In one particular embodiment, naturally occurring pectin is modified as to replace the hydroxyl groups at the $C_2$ and $C_3$ positions of galacturonic acid with O-acetyl groups. The modified pectin is referred to herein as OAcPec. The characteristics of OAcPec in comparison with Vi of *S. typhi* is as follows:

1) the $M_1$ of Vi (~$2\times10^3$ kD) is higher than that of OAcPec (~400 kD); 2) the N-acetyl at $C_2$ in the Vi is replaced by an O-acetyl in OAcPec and; 3) OAcPec has <5% neutral sugars and Vi had a nondetectable amount. At 3°–8° C., the stability of OAcPec as measured by its O-acetyl content and molecular size, is similar to that of Vi. At higher temperatures, the molecular size of Vi is more stable than the OAcPec probably due to the stabilizing effect of a hydrogen bond between the N-acetyl and the carboxyl of the adjacent residue [23]. Since vaccines will be stored at ≦3°–8° C., the stability characteristic of OAcPec and Vi can be considered as similar.

Figure 4:
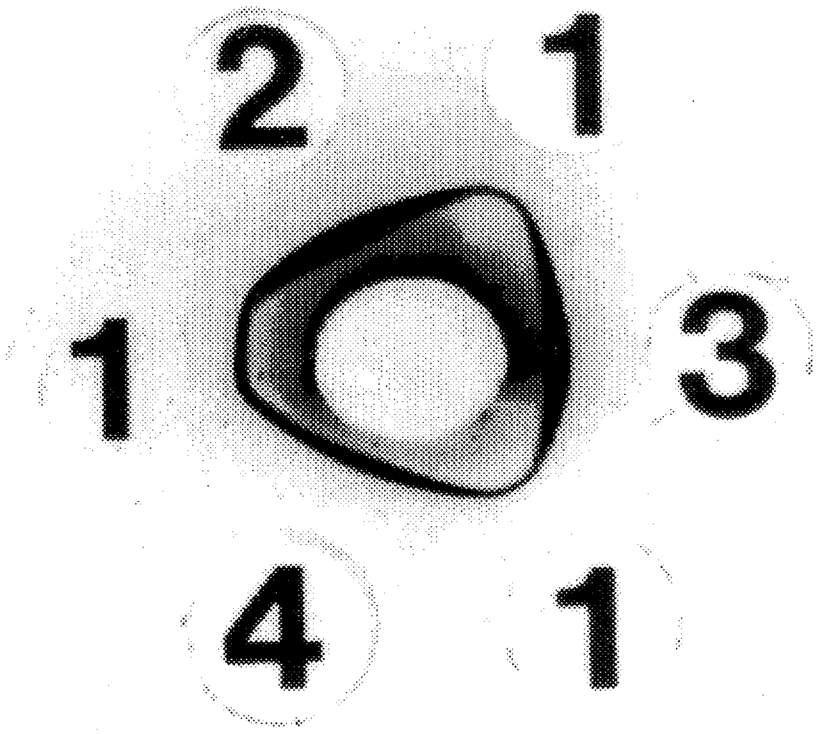
FIG. 4 shows the antigenicity of the O-acetylated pectin compared with Vi by double immunodiffusion. Center well, B-260 Vi antiserum, 1) Vi, 100 μg/ml; 2) OAcPec $K^+$ form; 3) OAcPec $Ca^{++}$ form; 4) OAcPec $C_2H_5N^+$ form.

OAcPec and Vi are antigenically indistinguishable by immunodiffusion (FIG. 4). However, OAcPec, unlike Vi, is not immunogenic in mice probably due to its lower molecular weight [16].

Another embodiment of the present invention is a modified pectin, and modified D-galacturonan, oligo-, and polygalacturonate-carrier conjugate. The modified pectin and modified D-galacturonan, oligo-, and polygalacturonate-carrier conjugate is immunogenic to Vi in mammals. By immunogenic is meant that the modified pectin-carrier conjugate and modified D-galacturonan, oligo-, and polygalacturonate-carrier conjugate elicit the production of antibodies upon injection into mammals. The antibodies elicited are capable of specifically reacting or binding to *S. typhi*, are capable of specifically reacting or binding to the Vi of *S. typhi* and are capable of providing passive protection against *S. typhi* in humans. The modified pectin and modified D-galacturonan, oligo-, and polygalacturonate-carrier conjugate of the present invention are capable of inducing a statistically significant rise of antibodies that bind to Vi (booster effect) upon reinjection.

Modified pectin, and modified D-galacturonan, oligogalacturonate and modified polygalacturonate have several advantages over the Vi in preparing conjugates for vaccines to prevent typhoid fever. Special P3 facilities are required to culture pathogens such as *S. typhi*. This restricts the availability of Vi and presents safety concerns in preparing a Vi vaccine. The present invention of 1) pectin, D-galacturonan, oligo- and polygalacturonate are easy to obtain, safe and purification is simpler than extraction of the Vi from *S. typhi*; 2) modified oligo- and polygalacturonate can be measured during the synthesis of the conjugate and in the final container by a colorimetric reaction and; 3) there is no solubility problem and the yield of modified pectin, D-galacturonan, oligo- and polygalacturonate-carrier conjugates is higher than with Vi; 4) at the 4° C., the standard storage temperature of vaccines, the stability of modified pectin, D-galacturonan, oligo- and polygalacturonate is similar to that of the Vi.

The present invention provides method to prepare a synthetic Vi antigen from a plant, fruit or synthetic oligo- or polysaccharide and to conjugate it with a carrier in order to enhance and elicit a booster response against *Salmonella typhi* capsular polysaccharide.

In one embodiment of the method, pectin, D-galacturonan, oligogalacturonate, or polygalacturonate is O-acetylated at C2 and C3 positions with acetic anhydride. Through carbodimide condensation the O-acetylated pectin, D-galacturonan, oligogalacturonate, or polygalacturonate is thiolated with cystamine, or aminolated with adipic dihydrazide, diaminoesters, ethyldiamine and the like. Both the thiolated and the aminolated O-acetylated pectin, D-galacturonan, oligogalacturonate, or polygalacturonate are stable, may be freeze dried, and stored in cold. The thiolated intermediate may be reduced and covalently linked to a polymeric carrier containing a sulfhydro group, an N-pyridyldithio group. The aminolated intermediate may be covalently linked to a polymeric carrier containing a carboxyl group through carbodiimide condensation. The O-acetylated pectin, D-galacturonan, oligogalacturonate, or polygalacturonate covalently linked to a polymeric carrier is immunogenic in mammals and can serve as a typhoid fever vaccine.

Purification and O-acetylation of a plant or fruit polysaccharide:

Pectin extracted and purified from plants or fruits such as, but not exclusive, inner portion of the rind of citrus fruits such as oranges, fruit pomaces as from apples or beets, and the like, can be used as the source of polysaccharide. The pectin may be further purified, for example, by precipitation with ethanol or gel filtration and the like. Pectin can be O-acetylated by treatment with acetic anhydride in formamide and pyridine. The content of O-acetyl groups can be increased by repeat the acetylation process until the desired level of acetylation is achieved.

Polymeric carriers:

Carriers are chosen on the basis of facilitating two functions: 1) to increase the immunogenicity of the polysaccharide and 2) antibodies raised against the carrier are medically beneficial. Carriers that fulfill these criteria are described in the art (7, 10, 22–25). Polymeric carriers can be a natural or a synthetic material containing a primary or/and a secondary amino group, an azido group or a carboxyl group. The carrier can be water soluble or insoluble. Examples of water soluble carriers included but are not limited to natural or synthetic peptides or proteins from bacteria or virus, e.g., tetanus toxin/toxoid, diphtheria toxin/toxoid, *Pseudomonas aeruginosa* exotoxin/toxoid/protein, pertussis toxin/toxoid, *Clostridium perfringens* exotoxins/toxoid, and hepatitis B surface antigen and core antigen. Example of water insoluble carriers include but are not limited to are aminoalkyl-Sepharose, e.g., aminopropyl or aminohexyl Sepharose, and aminopropyl glass and the like. Other carriers may be used when an amino or carboxyl group is added through covalent linkage with a linker molecule.

Synthesis of O-acetylated pectin, D-galacturonan, oligogalacturonate, or polygalacturonate conjugated with a carrier:

The O-acetylated pectin, D-galacturonan, oligogalacturonate, or polygalacturonate can be covalently bound to a carrier with or without a linking molecule. To conjugate without a linker, the O-acetylated pectin, D-galacturonan, oligogalacturonate, or polygalacturonate and carrier are mixed in the presence of carboxyl activation agent, such as carbodiimide in a choice of solvent appropriate for both the pectin, D-galacturonan, oligogalacturonate, or polygalacturonate and the carrier as are known in the art. (24)

The O-acetylated plant, fruit or synthetic D-galacturonan, oligosaccharide or polysaccharide is preferably conjugated to a carrier using a linking molecule. A linker or crosslinking agent, as used in the present invention, is a small linear molecule having a molecular weight of approximately <500 and is non-pyrogenic and non-toxic in the final product form (7, 10, 22–25). To conjugate with a linker or crosslinking agent, either or both of the pectin, D-galacturonan, oligogalacturonate, or polygalacturonate and the carrier are covalently bound to a linker first. The linkers or crosslinking agents are a homobifunctional or heterobifunctional molecules, e.g., adipic dihydrazide, ethylene diamine, cystamine, N-succinimidyl-3-(2-pyridyldithio) propionate (SPDP), N-succinimidyl N-(2-iodoacetyl)-b-alaninate-propionate (SIAP), succinimidyl 4-(N-Maleimido-methyl) cyclohexane-1-carboxylate (SMCC), 3,3'-dithiodipropionic acid and the like. The linkers are bound to the carboxyl groups of the O-acetylated pectin, D-galacturonan, oligogalacturonate, or polygalacturonate or the carrier through carbodiimide condensation. The linkers are bound to the amino groups of the carrier through carbodiimide condensation or N-hydroxylsuccinimidyl ester. The unbound materials are removed by gel filtration or ion exchange column depending on the materials to be separated. The final conjugate consist of the oligo- or polysaccharide and the carrier bound through a linker.

Clinical evidence has shown that serum antibodies to the Vi antigen confers immunity to typhoid fever. (1,2). The immunogen used to elicit the antibodies was the Vi capsular polysaccharide. Because Vi antibodies have been shown to be protective against typhoid fever and due to the complexity and safety issues that arise from culturing *S. typhi*, the World Health Organization (WHO) and the U.S. Food and Drug Administration (FDA) no longer require challenge data as criteria for licensing an acellular vaccine against *Salmonella typhi* (32). WHO and FDA criteria for licensing an acellular vaccine against *Salmonella typhi* is the demonstration that the preparation elicits Vi antibodies or that the preparation binds to Vi antibodies.

The modified pectin-carrier conjugates and modified D-galacturonan, oligogalacturonate and polygalacturonate-carrier conjugates of the present invention elicit antibodies that react with or bind to the Vi antigen. The anti-Vi antibody levels elicited by the modified pectin-carrier conjugates were comparable to those elicited by a Vi-*Pseudomonas aeruginosa* recombinant exoprotein A (rEPA) conjugate as measured by ELISA. Thus, the modified pectin-carrier and modified D-galacturonan, oligogalacturonate and polygalacturonate-carrier conjugate may be used as an effective vaccine against *S. typhi* to prevent or ameliorate typhoid fever in humans.

The present inoculum contains an effective, immunogenic amount of modified pectin-carrier conjugate and modified D-galacturonan, oligogalacturonate and polygalacturonate-carrier conjugates of this invention. The effective amount of modified pectin-carrier conjugate and modified D-galacturonan, oligogalacturonate and polygalacturonate-carrier per unit dose sufficient to induce an immune response to the Vi antigen depends, among other things, on the species of mammal inoculated, the body weight of the mammal and the chosen inoculation regimen as is well known in the art. Inocula typically contain modified pectin-carrier conjugate and modified D-galacturonan, oligogalacturonate and polygalacturonate-carrier conjugate concentrations of oligo- or polysaccharide of about 1 micrograms to about 100 milligrams per inoculation (dose), preferably about 25 micrograms to about 50 milligrams per dose.

The term "unit dose" as it pertains to the inocula refers to physically discrete units suitable as unitary dosages for mammals, each unit containing a predetermined quantity of active material (oligo- or polysaccharide) calculated to produce the desired immunogenic effect in association with the required diluent. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared as a solution in tolerable (acceptable) diluent such as water, saline or phosphate-buffered saline or other physiologically tolerable diluent such as water and the like to form an aqueous pharmaceutical composition.

The route of inoculation may be intramuscular, subcutaneous and the like, which results in eliciting antibodies protective against *S. typhi*. The dose is administered at least once. In order to increase the antibody level, a second or booster dose may be administered approximately 4 to 6 weeks after the initial injection. Subsequent doses may be administered as indicated.

Testing of the modified pectin-carrier conjugate and modified D-galacturonan, oligogalacturonate, and a polygalacturonate-carrier vaccines is conducted as prescribed by the World Health Organization as described in Example 6 or by any equivalent immunological assay. Elicitation of Vi antibodies is predictive of in vivo efficacy of the conjugates in humans. Antibodies elicited by the modified pectin-carrier conjugates and modified D-galacturonan, oligogalacturonate and polygalacturonate-carrier conjugates are useful in providing passive protection to an individual exposed to *S. typhi* to prevent or ameliorate infection and disease caused by the microorganism.

The term antibody in its various grammatical form is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', $F(ab')_2$ and F(v) as well as chimeric antibody molecules.

An antibody combining site or antigen binding fragment is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

An antibody of the present invention, i.e., an anti-Vi antibody, in one embodiment is characterized as comprising antibody molecules that immunoreact with: 1) *S. typhi* and 2) isolated Vi antigen of *S. typhi*. In another embodiment the antibody is characterized as comprising antibody molecules that immunoreact with: 1) *S. typhi*, 2) isolated Vi antigen of *S. typhi* and 3) a modified pectin of the present invention, and being substantially free of antibody molecules that immunoreact with native or naturally occurring pectin.

An antibody of the present invention is typically produced by immunizing a mammal with an inoculum containing a modified pectin-carrier conjugate and modified D-galacturonan, oligogalacturonate and polygalacturonate-carrier conjugates of this invention and thereby induce in the mammal, antibody molecules having immunospecificity for the immunizing conjugate. The antibody molecules are then collected from the mammal. The antibody molecules of the present invention may be polyclonal or monoclonal antibody. Monoclonal antibodies may be produced by methods known in the art. The antibody of the present invention may be contained in blood plasma, serum, hybridoma supernatants and the like. Alternatively, the antibody of the present invention is isolated to the extent desired by well known techniques such as, for example, by using DEAE Sephadex. The antibodies may be purified so as to obtain specific classes or subclasses of antibody such as IgM, IgG, IgA, $IgG_1$, $IgG_2$, $IgG_3$, $IgG_4$ and the like. Antibody of the IgG class are preferred for purposes of passive protection.

The antibodies of the present invention have a number of diagnostic and therapeutic uses. The antibodies can be used as an in vitro diagnostic agent to test for the presence of *S. typhi* in biological samples in standard immunoassay protocols. Such assays include, but are not limited to, radioimmunoassays, EIA, fluorescence assay, Western blot and the like. In one such assay, the biological sample is contacted to antibodies of the present invention and a labelled second antibody is used to detect the presence of *S. typhi*, or the Vi antigen of *S. typhi* to which the antibodies are bound.

Such assays may be, for example, of direct format (where the labelled first antibody is reactive with the antigen), an indirect format (where a labelled second antibody is reactive with the first antibody), a competitive format (such as the addition of a labelled antigen), or a sandwich format (where both labelled and unlabelled antibody are utilized), as well as other formats described in the art.

The antibodies and antigen binding fragments of the present invention are useful in prevention and treatment of infections and diseases caused by *S. typhi* and other microorganisms that have structures immunologically similar to the Vi antigen.

In providing a patient with the antibodies or antigen binding fragments of the present invention to a recipient mammal, preferably a human, the dosage of administered antibodies or antigen binding fragments will vary depending upon such factors as the mammal's age, weight, height, sex, general medical condition, previous medical history and the like.

In general, it is desirable to provide the recipient with a dosage of antibodies or antigen-binding fragments which is in the range of from about 1 mg/kg to about 10 mg/kg body weight of the mammal, although a lower or higher dose may be administered.

The antibodies or antigen-binding fragments of the present invention are intended to be provided to the recipient subject in an amount sufficient to prevent, lessen or attenuate the severity, extent or duration of the infection by *S. typhi.*

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided either prior to the anticipated exposure to *S. typhi* (so as to attenuate the anticipated severity, duration or extent of an infection and disease symptoms) or after the initiation of the infection.

For all therapeutic, prophylactic and diagnostic uses, the modified pectin, modified D-galacturonan, oligogalacturonate, polygalacturonate, alone or linked to a carrier, as well as antibodies and other necessary reagents and appropriate devices and accessories may be provided in kit form so as to be readily available and easily used.

EXAMPLE 1

Materials and Methods

Reagents:

Pectin (GENU pectin, from Copenhagen, Denmark, type LM-1912CSZ) was extracted from citrus. Pyrogen-free water (PFW) and pyrogen-free saline (PFS) for clinical use were from Baxter, Deerfield, Wis.; N-succinimidyl 3(2-pyridyldithio) propionate (SPDP) from Pierce, Rockford, Ill.; formamide, cystamine from Fluka, Ronkoncoma, N.Y.; pyridine, NaOH, HCl from Baker Chemical, Philipsburg, N.J., acetic anhydride, dithiothreitol (DTT), EDTA, 1-ethyl-3(d-dimethylaminopropyl) carbodimide (EDAC), acetyl choline, BSA, dithionitrobenzoic acid (Ellman reagent), D-galacturonic acid monohydride (GalA) and tetrabutylammonium hydroxide from Sigma, St. Louis, Mo.; carbazole from Aldrich, Milwaukee, Wis.; HEPES from Calbiochem, La Jolla, Calif.; bicinchoninic acid (BCA) protein reagent, Sephacyl S-1000, Sephadex G-50, Superose 6 from Pharmacia, Piscataway, N.J. Antiserum to tetanus toxoid (TT) was donated by William Habig, CBER, FDA. Pseudomonas aeruginosa exotoxin A (ETA) and goat antiserum to this protein were from List Biological Lab., Campbell, Calif., Vi antiserum (B-260) was prepared by multiple intravenous injections of a burro with heat-killed *S. typhi* strain Ty-2[19]. *Pseudomonas aeruginosa* recombinant exoprotein A (rEPA) was made as described in U.S. Ser. No. 08/189,113 filed Jan. 27, 1994, which is a continuation of U.S. Ser. No. 07/825,089 filed Jan. 24, 1992, abandoned. The Vi-rEPA was made as described in U.S. Pat. No. 5,204,098 issued Apr. 20, 1993.

Analytic:

The molecular sizes of polysaccharides and conjugates were measured with Superose 6 HPLC column in 0.02M sodium phosphate buffer containing 0.1M $Na_2SO_4$ a pH 7.0. Carboxyls were measured by the carbazole reaction with pectin as a standard [3,27]. O-acetyl was measured with acetyl choline as a standard and the results expressed as moles/mole GalA [12]. The concentration of sulfhydryl was determined by Ellman reaction [8]. Protein was determined with BCA with BSA as a standard [20]and the content of nucleic acids was determined by $A_{260}$ [28]. $^{13}C$ nuclear magnetic resonance spectroscopy (NMR) was performed with a General Electric GN300 spectrometer at room temperature [23].

EXAMPLE 2

Preparation of O-Acetylated pectin from citrus

Pectin was dissolved in PFW (10 mg/mL) at 60° C. for 1 hour, cooled to room temperature and adjusted to pH 7.0 with 1M NaOH. The polysaccharide was precipitated twice with 75% ethanol and then freeze-dried. Pectin so treated contained less than 1% of protein and nucleic acid [28]. O-acetylation of pectin was performed as described [6]. Briefly, pectin (1 g) was suspended in formamide (20 mg/mL) at 50° C. for 1 hour, 20 mL pyridine added, mixed and cooled to room temperature. Acetic anhydride (15 mL) was added dropwise with mixing at room temperature for 2 hours. The reaction mixture was poured into cold absolute ethanol. The precipitate was filtered, dissolved in PFW and dialyzed at 3 to 8° C. against multiple changes of deionized water and freeze-dried. The degree of O-acetylation was about 50%, compared to the maximum possible yield of 200%. In order to reach a higher degree of O-acetylation, the OAcPec was subjected again to the same procedure. The final product was passed through a 2.5×50 cm column of Sephadex G-50 in PFW and the void volume peak was passed through a sterile 0.45 micron membrane and freeze-dried. This preparation contained ~1.6 moles of O-acetyl/mole GalA or 80% yield.

Figure 2:
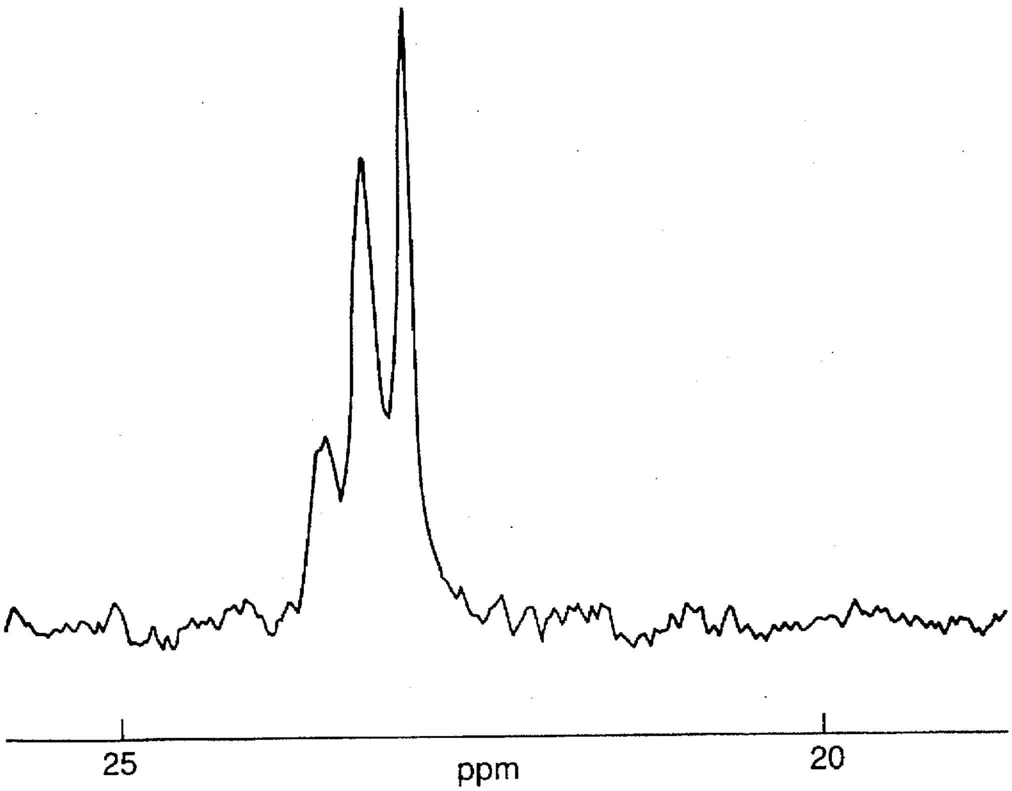
FIG. 2 shows the methyl resonances on the O-acetylated pectin by $^{13}C$ NMR spectroscopy

The molar content of the O-acetyl groups are determined by Hestrin reaction (12). The distribution of the O-acetyl groups are studied by the methyl resonances of $^{13}C$ NMR spectroscopy (FIG. 2).

The antigenicity of the O-acetylated pectin was studied by reaction with the antiserum against *Salmonella typhi* in 2-dimensional immunodiffusion using Vi polysaccharide as a comparison. Immunodiffusion was performed in 1% agarose in PBS with B-260 antiserum. Quantitative precipitation was performed with 100 μL of B-260 with equal volumes of antigen, containing 1 to 100 μg/mL, at 37° C. for 1 hour and at 3°–8° C. for five days with occasional mixing. The precipitates were washed in cold PFS three times, dissolved in 0.8% SDS and their $A_{280}$ recorded [23]. Serum Vi antibodies were measured by ELISA using a pooled hyperimmune mouse sera, quantitated by radioimmunoassay, as the standard [1].

The stability of the O-acetyl groups are studied at various temperatures for various periods of time. OAcPec and Vi (1 mg/mL) in PBS, pH 7.0, were incubated at 3°–8° C., 25° C., 37° C. and 60° C. Aliquots were removed at 1, 2, and 12 wks and analyzed for their content of O-acetyl and molecular size by gel filtration.

EXAMPLE 3

Preparation of conjugates

The synthesis of conjugates followed that described for Vi [24]. The polysaccharide (5 mg/mL) was dissolved in 0.2M NaCl. Cystamine (0.1M) was added and the pH adjusted to 5.0 with 0.1M HCl. The temperature was 37° C. for Vi and room temperature for OAcPec. EDAC (0.1M) was added and the reaction mixture stirred for 4 hours with the pH maintained between 4.9 to 5.1. The reaction mixture was dialyzed against PFS with 10 mM phosphate, pH 7, 3°–8° C. for one day, against PFW for 3 days with multiple changes and freeze-dried. Thiolation was measured on an aliquot of the polysaccharides treated with 0.1M DTT at room temperature for 1 hour and passage through a 2.5×35 cm P10 column. Void volume fractions were titrated for their sulfhydryl content and the degree of derivatization expressed as percent cystamine.

Derivatization of proteins with SPDP. SPDP, in absolute ethanol, was added dropwise at room temperature with stirring to protein (5 mg/mL) in 0.15M HEPES, 0.001M EDTA, pH 7.5 (HE buffer) to a final concentration of 0.04M. The reaction proceeded for 1 hour and dialyzed against the HE buffer overnight. The reaction mixture was passed through a 2.5×35 cm column of P10 in HE buffer and the void volume fractions concentrated to ~10 mg/mL. An aliquot was treated with 0.075M DTT at room temperature for 2 hours and its $A_{343}$ used to calculate the molar ratio of SPDP to protein [5].

Conjugation reaction.

The cystamine-derivatized polysaccharide, 10 mg/mL PBS, pH 7.4, was treated with 0.05M DTT at room temperature for two hours and passed through a 2.5×35 cm column of Sephadex G-50 in PBS, pH 7.0. An aliquot was taken to determine its sulfhydryl content and the remainder mixed with an equal weight of SPDP-derivatized protein and stirred at room temperature for 4 hours and at 3°–8° C. overnight. The reaction mixture was passed through a 2.5×95 cm column of Sephacryl S-1000 in PFS at 3°–8° C. For the OAcPec-TT, fractions containing protein and polysaccharide were pooled into two batches: OAcPec-$TT_1$ for the void volume peak and OAcPec-$TT_2$ for the lower molecular weight fractions. Vi-rEPA was passed through a 2.5×95 cm column of Sephacryl S-1000 in PFS and the void volume fractions pooled.

EXAMPLE 4

Characterization of O-acetylated pectin

Physico-chemical characterization of OAcPec:

O-acetylation ranged from 0.1 to 1.6 moles/GalA for pectins. Unless specified, the OAcPec described in the following had 1.6 mole O-acetyl/mole GalA. [b] $^{13}C$ N.M.R. of OAcPec showed more than two signals observed with acetyl methyl resonances indicating that mono and diacetylated species are present: non-O-acetylated residues could, however, be present (FIG. 2). The stoichiometry of $C_2$ and $C_3$ O-acetylation are the same. Therefore, the O-acetyl groups are probably distributed equally between $C_2$ and $C_3$ (FIG. 2), at least 60% of the GalA are di-O-acetylated, while 20% are mono-O-acetylated. Neutral sugar content in the pectin is lower than 5%.

Figure 3:
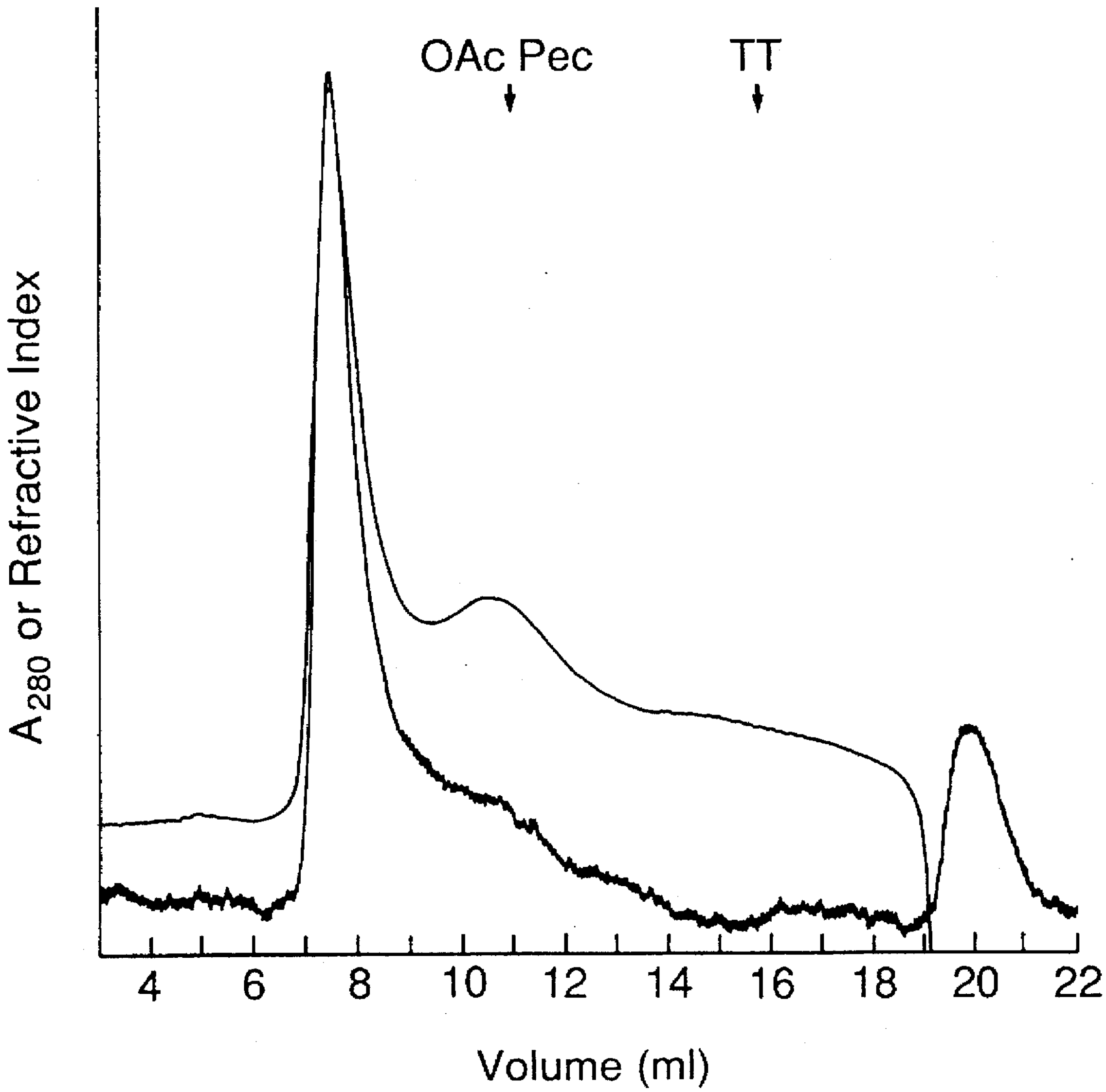
FIG. 3 shows the HPLC gel filtration profile of the O-acetylated pectin –TT conjugate through Superose 6 in 0.01 sodium phosphate, 0.1M Na2SO4, pH 7.0. The refractive index is the upper line and the 280 nm absorbance is the lower line.

The $M_r$ of OAcPec, similar to that of the pectin, had a broad distribution with the major peak ~400 kD (FIG. 3). Unlike pectin, OAcPec was soluble in 0.15M NaCl and did not form a gel in the presence of $Ca^{++}$. Molar absorbances in the carbazole assay were 1.32×10 for OAcPec, $1.61\times10^3$ for pectin and $1.63\times10^3$ for GalA. The differences between pectin and GalA were <2% and are probably due to neutral sugars in the pectin. Vi, in contrast, did not react in the carbazole assay.

Figure 5:
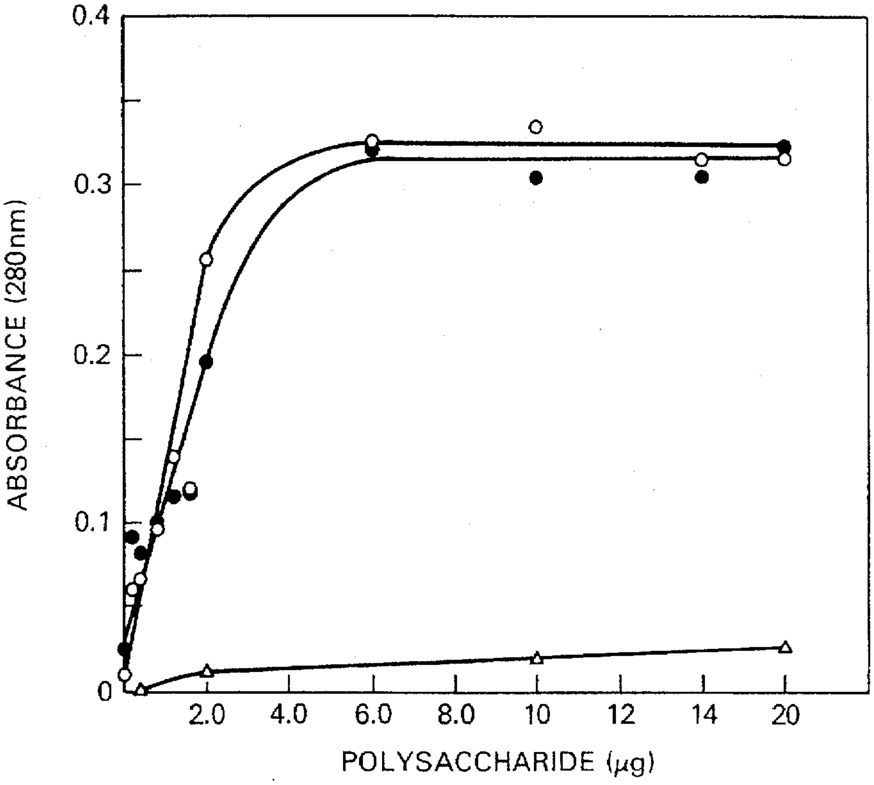
FIG. 5 shows the quantitative precipitin analysis of pectin (Δ), OAcPec (o) and Vi (O).

Pectin did not react with B-260 serum in double immunodiffusion. OAcPec, in contrast, formed a line of identity with Vi (FIG. 4). Precipitation of OAcPec with Vi antiserum did not change with different counter ions including $Na^+$, $Ca^{++}$, $K^+$ or tetrabutylammonium. At lower degrees of O-acetylation (0.4–0.9 moles O-acetyl/mole GalA) pectin also yielded a line of identity with the Vi (not shown). No precipitation in double immunodiffusion was observed when the O-acetylation of pectin was ≦0.2 mole/mole GalA. Quantitative precipitation showed that both Vi and OAcPec precipitated 2.6 mg/mLAb from B-260 antiserum (FIG. 5).

Stability of OAcPec and Vi O-acetyls

Figure 6:
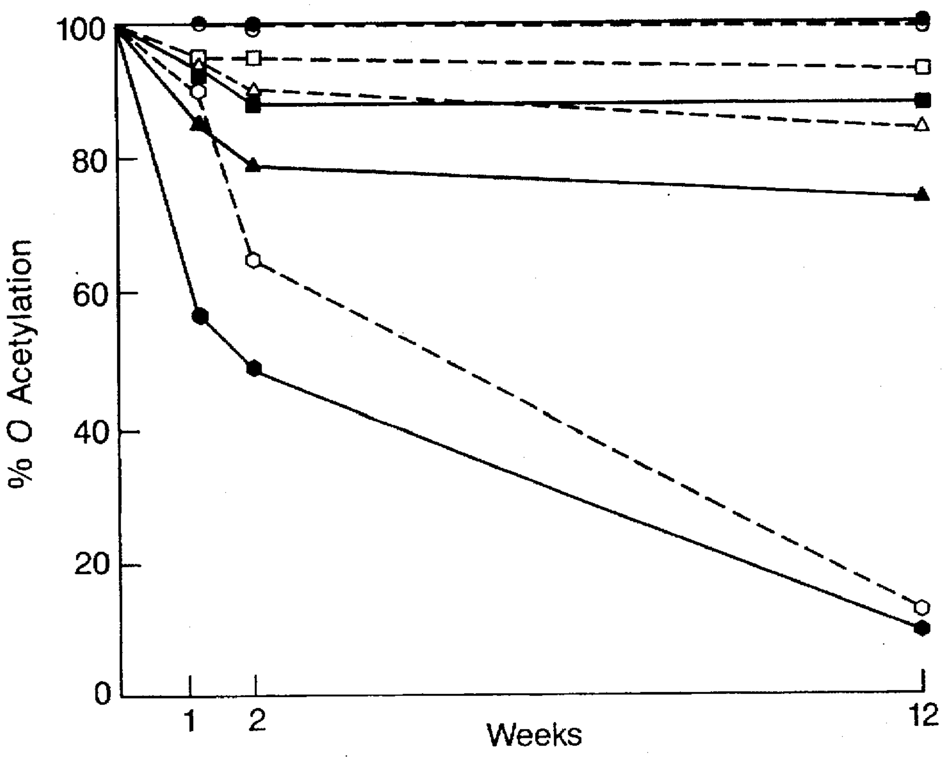
FIG. 6 shows the temperature dependent stability of O-acetyls on Vi at 4° C. (0—0), Vi at 22° C. (□—□), Vi at 37° C. (Δ—Δ), Vi at 60° C. (◇—◇), OAcPec at 4° C. (●—●), OAcPec at 22° C. (■—■), OAcPec at 37° C. (▲—▲) and OAcPec at 60° C. ♦—♦). The decrease in extent of O-acetylation is depicted as the % remaining after incubation at the various intervals and temperatures compared to the starting material.

The thermostability of the O-acetyls was similar for OAcPec compared to Vi (FIG. 6). Following storage at 3°–8° C. for 12 weeks, there was no change in the concentration of O-acetyls for Vi and OAcPec compared to the original level of O-acetyls for Vi and OAcPec prior to storage: at 22° C., O-acetyls declined to 93% for Vi and to 88% for OAcPec and at 60° C., only 12% of the O-acetyls remained on Vi and 10% on OAcPec.

Molecular size.

The stabilities of glycosidic linkages of the polysaccharides were studied by gel filtration. There was no change in $M_r$ of OAcPec at 3°–8° C. for three months. After storage of OAcPec at 60° C. for three month, the $M_r$ decreased from 400 kD to 30 kD (not shown). In contrast, the Vi was more stable: little depolymerization was observed after incubation at 60° C. for two weeks and the $M_r$ shifted from $2\times10^3$ kD to 500 kD after 3 months.

EXAMPLE 5

Characterization and immunogenicity of the conjugate

The degree of thiolation was 4% for the O-acetylated pectin. The HPLC profile of OAcPec-TT shows the conjugate and a small portion of OAcPec were eluted in the void volume (FIG. 3). In several experiments (not shown) the final yield of the conjugate was 20–30%. The polysaccharide-protein ratio is ~0.4–0.8% wt/wt.

TABLE 1

Composition of conjugates of O-acetylated pectin (OAcPec) with tetanus toxoid (TT) and Vi with *Pseudomonas aeruginosa* recombinant Exoprotein A (rEPA).

| Conjugate | $M_r$ Ps (kD) | Cysteamine/ PS (%) | SPDP/protein molar ratio | Ps/protein ratio (wt/wt) |
|---|---|---|---|---|
| OAcPect-$TT_1$ | 400 | 4.0 | 3.6 | 0.4 |
| OAcPect-$TT_2$ | 400 | 4.0 | 3.6 | 0.8 |
| Vi-rEPA | $2 \times 10^3$ | 1.3 | 2.1 | 0.2 |

Immunization:

16–20 g ♀ general purpose mice from the NIH colony were injected subcutaneously 1, 2, or 3 times at 2 week intervals with 2.5 μg of the polysaccharide alone or as a conjugate. 10 mice from each group were exsanguinated two weeks after the first injection and one week after the second and third injections. Controls included mice injected with saline, Vi or OAcPec. Vi antibody levels were measured by ELISA with a reference calibrated by RIA.

ELISA Procedure for the Measurement of Vi Antibody

Reagents:

Vi antigen purified from *S. typhi*, alkaline phosphatase labeled goat anti-mouse or alkaline phosphatase labeled anti-human (Kirkegaard & Perry Lab. Inc.)=Conjugate; -p-nitrophenyl phosphate disodium (Sigma Fine Chemical)= Substrate; bovine serum albumin (BSA) (Sigma Fine Chemical); sodium carbonate ($Na_2CO_3$); sodium bicarbonate ($NaHCO_3$); sodium chloride; Brij 35; Na $N_3$; Tris-HC-$MgCl_2$; HCl; PBS.

Buffers:

Coating Buffer: sodium carbonate-sodium bicarbonate buffer solution, pH 9.5 at 20° C., 30 ml 0.1M $Na_2CO_3$, 70 ml 0.1M $NaHCO_3$.

Washing Buffer: 0.85% NaCl, 0.1% Brij 35, 0.02% $NaN_3$.

Dilution Buffer: 1×PBS, 0.1% Brij 35, 2% BSA, prepare fresh each time, filter with 0.45 μm Millipore filter. Dilution buffer without BSA (DB) can be prepared as a "stock solution" and BSA added before use.

Substrate Buffer: 1000 ml Tris-HCl300 ml 1MMg$Cl_2$, adjust pH to 9.8 with HCl.

Conjugate Buffer: is the same as DB.

Procedure:

1. Store frozen Vi polysaccharide (0.1 mg/ml) 500 μl aliquots.
2. Coat microtiter plates (96 well, flat bottom, polystyrene Immunolon microtiter plates) with Vi. Dilute 1 to 2 μg Vi per ml in "coating buffer" use 100 μl/well, shake gently. Incubate plates at 4° C. overnight covered with polyester film.
3. Wash plates twice in "washing buffer", shake dry.
4. Dilute antibody samples in dilution buffer DB.BSA. Dilution factor may be 5 to 10.
5. Make serial dilutions in the plate, pipet 100 μl of DB.BSA in all wells except for the first row. Deliver 200 μl of the diluted sample in the first row. Transfer 100 μl subsequently from the top row down, use the multichannel pipet to mix in the wells. Remove the excess 100 μl from the bottom row.
6. Incubate the antigen-antibody mixture at room temperature overnight.
7. Wash plates twice.
8. Add 100 μl/well conjugate diluted 1:500 to 1:1000 in DB and incubate at 37° C. for 4 hours.
9. Wash plates twice.
10. Add 100 μl/well phosphatase substrate (1 mg/ml) freshly prepared in substrate buffer. Add it to each vertical row every 6 seconds, 3 minute interval between each plate.
11. Read plates at 410 nm approximately 15–20 minutes after the addition of the substrate. Sometimes the plates should be read at various time durations depending on the concentration and strength of the conjugate. Optimum optical density should be between 1.0 and 1.5.

Statistical:

Logarithms of antibody concentrations were used for all calculations. Antibody concentrations below the sensitivity of the ELISA were assigned one half of that value. Comparisons of geometric means were performed by unpaired t-tests. The Statistical Analysis System (SAS) was used for all data analyses.

Vi antibodies:

As reported, Vi elicited serum antibodies in mice after one injection and reinjection did not elicit a booster response [14,22–25]. Neither the pectin nor the OAcPec elicited Vi antibodies after any injections. After one injection, the Vi and OAcPec conjugates elicited similar levels of antibodies. Following the second injection, the conjugates elicited a booster response ($P<0.001$) with the geometric mean antibody levels highest for Vi-rEPA (17.1) >OAcPec-$TT_2$ (7.65) >OAcPec-$TT_1$ (5.47). These differences, however, were not statistically significant. The third injection of all 3 conjugates did not elicit a booster response. Lastly, there were no statistically significant differences in the geometric mean (GM) Vi antibody levels elicited by OAcPec-$TT_1$ and OAcPec$TT_2$ after any of the three injections.

TABLE 2

Vi antibodies (μg Ab/mL serum) in mice immunized with Vi, Vi-rEPA, Pectin, O-acetyl Pectin (OAcPec) and OAcPec-TT conjugates.

| | Geometric Mean [n = 10] | | |
|---|---|---|---|
| Immunogen | 1st Injection | 2nd Injection | 3rd Injection |
| Vi | 0.65 | 0.76 | Not Done |
| Vi-rEPA | $0.85^a$ | $17.1^b$ | $12.7^c$ |
| Pectin | <0.03 | <0.03 | Not Done |
| OAcPec | <0.03 | 0.04 | Not Done |
| OAcPec-$TT_1$ | $0.98^d$ | $5.47^e$ | $6.29^f$ |
| OAcPec-$TT_2$ | $0.87^g$ | $7.65^h$ | $5.29^i$ |

b, c vs a, P = 0.0002, f,e vs d, P = 0.0001, h vs g, P = 0.0002, i vs g, P = 0.007, b vs c, f vs e, h vs i, b vs e or h, c vs f,i, NS.

EXAMPLE 6

WHO Testing Protocol of *S. typhi* Vaccines

The modified pectin, modified D-galacturonan, oligogalacturonate and polygalacturonate-carrier conjugates vaccines are tested as per WHO requirements for acellular vaccines against *Salmonella typhi* (32).

The following tests are carried out on each lot of modified saccharide-carrier conjugate vaccine as per WHO requirements as briefly outlined:

1) serological testing for immunological identify with a standardized Vi antigen; 2) polysaccharide content; 3) sterility testing; 4) pyrogenicity testing; 5) toxicity testing; 6) preservative content (if added); 7) pH; and 8) stability studies.

Those lots fulfilling the WHO requirements are suitable for use in humans as a Salmonella typhi vaccine.

EXAMPLE 7

Human Vaccination Using A Modified Pectin-Carrier Conjugate

Volunteers between 18 and 45 years of age, who have no antibodies to hepatitis B and to HIV-1 are recruited. Following receipt of their informed consent, volunteers receive 1 injection of Vi (25 μg in 0.5 mL) (1,13) or 1 injection of a modified pectin-carrier conjugate (25 μg polysaccharide in 0.5 mL) of the present invention intramuscularly. Oral temperature is taken and the injection site of each volunteer is inspected 6, 24 and 48 hours after each injection. Volunteers receive a second injection at 6 weeks and are bled 2 weeks later and 26 weeks after the first injection. Antibodies reactive to Vi are determined by ELISA as described herein.

While the invention is described above in relation to certain specific embodiments, it will be, understood that many variations are possible, and that alternative materials and reagents can be used without departing from the invention. In some cases such variations and substitutions may require some experimentation, but some will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

All references and patents referred to are incorporated herein by reference.

REFERENCES

1. Acharya, I. L., C. U. Lowe, R. Tapa, V. L. Gurubacharya, M. B. Schrestha, M. Cadoz, D. Schulz, J. Armand, D. A. Bryla, B. Trollfors, T. Cramton, R. Schneerson and J. B. Robbins.
2. Avery, O. T., and W. F. Goebel. 1933. Chemoimmunological studies on the soluble specific substance of pneumococcus. I. The isolation and properties of the acetyl polysaccharide of pneumococcus type 1. *J. Exp. Med.* 58:731–755.
3. Bitter, T., and H. M. Muir. 1962. A modified uronic acid carbazole reaction. *Anal. Biochem.* 4:330–334.
4. Bystricky, S., and S. C. Szu. 1994. O-acetylation affects the binding properties of the carboxyl groups on the Vi bacterial polysaccharide *Biophys. Chem.* 51:1–7.
5. Carlsson, J., H. Drevin, R. Axen. 1978. Protein thiolation and reversible protein-protein conjugation. *Biochem. J.*173:723–737.
6. Carson, T. F., and W. D. Maclay. 1946. The acetylation of polyuronides with formamides as a dispersing agent. *J. Am. Chem. Soc.* 68:1015–1017.
7. Devi, S. J., J. B. Robbins and R. Schneerson. 1992. Antibodies to poly[(2→8)-α-N-acetylneuraminic acid] are elicited by immunization of mice with Escherichia coli K92 conjugates: Potential vaccines for groups B and C meningococci and *E. coli. Proc. Natl. Acad. Sci. USA* 88:7175–7179, 1991.
8. Ellman, G. L. 1959. Tissue sulfhydryl groups. *Arch. Biochem. Biophy.* 82:70–77.
9. Fass, R., M. van de Walle, A. Shiloach, A. Joslyn, J. Kaufman, and J. Shiloach. 1991. Use of high density cultures of *Escherichia coli* for high level production of recombinant *Pseudomonas aeruginosa* exotoxin *A. Appl. Microbiol. Biotechnol.* 36:65–69.
10. Fattom, A., C. Lue, S. C. Szu, J. Mestecky, G. Schiffman, D. Bryla, W. F. Vann, D. Watson, J. B. Robbins, and R. Schneerson. 1990. Serum antibody response in adult volunteers elicited by injection of the *Streptococcus pneumoniae* type 12F polysaccharide alone or conjugated to diphtheria toxoid. *Infect. Immun.* 58:2309–2312.
11. Heidelberger, M., and P. A. Rebers. 1960. Immunochemistry of the pneumococcal types II, V, and VI. I. The relation of type VI to type II and other correlations between chemical constitution and precipitation in antisera to type VI. *J. Bacteriol.* 80:145–153.
12. Hestrin, S. 1949. The reaction of acetylcholine and other carboxylic acid derivatives with hydroxylamine, and its analytical application. *J. Biol. Chem.* 180:249–261.
13. Klugman, K. P., H. J. Koornhof, I. T. Gilbertson, J. B. Robbins, R. Schneerson, D. Schulz, M. Cadoz, J. Armand, Vaccine Advisory Committee. 1987. Protective activity of Vi capsular polysaccharide vaccine against typhoid fever. Lancet ii:1165–1169.
14. Landy, M. 1957. Studies on the Vi antigen. VII. Characteristics of the immune response in the mouse. *Am. J. Hyg.* 65:81–93.
15. Landy, M. 1954. Studies in Vi antigen. VI. immunization of human beings with purified Vi antigen. *Amer. J. Hyg.* 60:52–62
16. Martin, D. G., F. G. Jarvis and K. C. Milner. 1967. Physicochemical and biological properties of sonically treated Vi antigen. *J. Bacteriol.* 94:1411–1416.
17. Peeters, C. A., A-M. Tenbergen-Meekes, D. E. Evenberg, J. T. Poolman, B. J. M. Zegers and G. T. Rijkers. 1991. A comparative study of the immunogenicity of pneumococcal type 4 polysaccharide and oligosaccharide tetanus toxoid conjugates in adult mice. *J. Immunol.* 146:4308–4314
18. Pilnik, W., and A. G. J. Voragen. 1970. Petic substances and other Uronides. In: The Biochemistry of Fruits and their Products, Vol. 1, pp. 53–73, Academic Press: New York.
19. Robbins, J. D., and J. B. Robbins. 1984. Protective role of the Vi capsular polysaccharide (Vi antigert) of *Salmonella typhi. J. Infect. Dis.* 47:436–499
20. Smith, P. K., R. I. Krohn, G. T. Hermanson, A. K. Mallia, F. H. Gartner, M. D. Provenzano, E. K. Fujimoto, N. M. Goeke, B. J. Olson, and D. C. Klenk. 1987. Measurement of protein using bicinchoninic acid. *Anal. Biochem.* 150:76–85.
21. Stone, A. L., and S. C. Szu. 1988. Application of optical properties of Vi capsular polysaccharide for quantitation of the Vi antigen in vaccines for typhoid fever. *J. Clin. Microbiol.* 26:719–725.
22. Szu, S. C., X. Li, R. Schneerson, J. H. Vickers, D. Bryla, and J. B. Robbins. 1989. Comparative immunogenicities of Vi polysaccharide-protein conjugates composed of cholera toxin or its B subunit as a carrier bound to high- or lower-molecular-weight Vi. *Infect. Immun.* 57:3823–3827.
23. Szu, S. C., X. Li, A. L. Stone, and J. B. Robbins. 1991. Relation between structure and immunologic properties of the Vi capsular polysaccharide. *Infect. Immun.* 59:4555–4561.
24. Szu, S. C., A. L. Stone, J. D. Robbins, R. Schneerson, and J. B. Robbins. 1987. Vi capsular polysaccharide-protein conjugates for prevention of typhoid fever. *J. Exp. Med.* 166:1510–1524.

25. Szu, S. C., D. N. Taylor, A. C. Trofa, J. D. Clements, J. Shiloach, J.C. Sadoff, D.A. Bryla and J. B. Robbins. 1994. Laboratory and preliminary clinical characterization of Vi capsular polysaccharide-protein conjugate vaccines. *Infect. Immun.* (in press).
26. Szewczyk, B., and A. Taylor. 1980. Immunochemical properties of Vi antigen from *Salmonella typhi* Ty2: Presence of two antigenic determinants. *Infect. Immun.* 29:539–544.
27. Taylor, K. A., and J. G. Buchanan-Smith. 1992. A colorimetric method for the quantitation of uronic acids and a specific assay for galacturonic acid. *Anal. Biochem.* 201:190–196.
28. World Health Organisation Expert Committee on Biological Standardization. 1977. Technical Report Series, 610. WHO, Geneva, Switzerland.
29. Gaines, S., J. A. Currie and J. G. Tully, 1960. Production of incomplete Vi antibody in mice. *Proc. Soc. Exp. Biol. Med.* 104:602.
30. Gaines, S., J. A. Currie and J. G. Tully, 1965. Production of incomplete Vi antibody in man by typhoid vaccine. *Am. J. Epidemiol* 81:350.
31. Kawata, Y. 1970. A study of the molecular types of immunoglobulin. II. Mouse protection study Vi antibody against typhoid infection. Acta *Medicine Univ. Kioto* 40: 284.
32. World Health Organization. 1994. Annex 1 Requirements for Vi polysaccharide typhoid vaccine (Requirements for Biological Substances No. 48) *WHO Technical Report Series* No. 840:14–33.

We claim:

1. A method to prepare an immunogenic modified plant, fruit or synthetic oligogalaturonate or polygalacturonate-carrier conjugate against *Salmonella typhi* comprising:

(a) O-acetylating a plant, fruit or synthetic oligogalacturonate or a polygalacturonate to form a modified plant, fruit or synthetic O-acetylated oligogalaturonate or a modified plant, fruit or synthetic O-acetylated polygalacturonate, (b) conjugating the modified plant, fruit or synthetic O-acetylated oligogalacturonate or the modified plant, fruit or synthetic O-acetylated polygalacturonate to a carrier to form the modified plant, fruit or synthetic oligogalacturonate or modified plant, fruit or synthetic polygalacturonate-carrier conjugate which is immunogenic against *Salmonella typhi.*

2. The method according to claim 1 wherein the O-acetylated oligogalacturonate or the O-acetylated polygalacturonate is at least 50% O-acetylated.

3. The method according to claim 1 wherein the O-acetylated oligogalacturonate or the O-acetylated polygalacturonate is about 80% to about 200% O-acetylated.

4. The method according to claim 1 wherein the O-acetylated oligogalacturonate or the O-acetylated polygalacturonate is about 160% to about 190% O-acetylated.

5. The method according to claim 1 wherein the method provides at least 0.5 mole of O-acetyl per mole of galacturonate of the O-acetylated oligogalacturonate or the O-acetylated polygalacturonate.

6. The method according to claim 1 wherein the method provides at least 1.6 moles of O-acetyl per mole of galacturonate of the O-acetylated oligogalacturonate or the O-acetylated polygalacturonate.

7. The method according to claim 1 wherein the method provides about 1.6 to about 1.9 moles of O-acetyl per mole of galacturonate of the O-acetylated oligogalacturonate or the O-acetylated polygalacturonate.

8. The method according to claim 1, wherein the acetylation occurs at a position on a galacturonic acid subunit of oligogalacturate or polygalacturate, the position selected from the group consisting of $C_2$, $C_3$,and both $C_2$, and $C_3$.

9. The method of claim 1 wherein the oligogalacturonate or polygalacturonate is pectin isolated from plants or fruits.

10. The method of claim 1 wherein the carrier is a protein selected from the group consisting of bacterial protein, viral protein, tetanus toxoid, tetanus toxin, diphtheria toxin, *Pseudomonas aeruginosa* exotoxin, *Pseudomonas aeruginosa* toxoid, pertussis toxin, pertussis toxoid, *Clostridium perfringens* exotoxin, *Clostridium perfringens* toxoid, hepatitis B surface antigen, hepatitis B core antigen and Pseudomonas exoprotein A.

11. The method of claim 1 wherein the carrier is a water insoluble carrier selected from the group consisting of aminoalkyl-Sepharose, amino propyl-Sepharose, aminohexyl-Sepharose, and amino propyl glass.

12. The method of claim 1 wherein the oligogalacturonate or polygalacturonate is O-acetylated in organic solvents with acetic anhydride.

13. The method of claim 1 wherein the O-acetylated oligogalacturonate or polygalacturonate is derivatized with a homobifunctional or a heterobifunctional cross-linking agent.

14. The method of claim 13 wherein the agent is selected from the group consisting of N-succinimidyl 3-(2-pyridyldithio) propionate, adipic dihydrazide, cystamine, 3,3' dithiodipropionic acid, ethylene diamine, N-(2-iodoacetyl)-b-alaninate-propionate and succinimidyl 4-(N-Maleimido-methyl) cycohexane-1-carboxylate.

15. A method according to claim 1 wherein the O-acetylated oligogalacturonate or O-acetylated polygalacturonate is thiolated and linked to a carrier containing a sulfhydro group.

16. A method according to claim 1 wherein the O-acetylated oligogalacturonate or O-acetylated polygalacturonate is aminolated and linked to a carrier containing a carboxyl group.

17. An immunogenic modified plant, fruit or synthetic oligogalacturonate or polygalacturonate carrier conjugate prepared according to the method of claim 1.

18. An immunogenic modified plant, fruit or synthetic oligogalacturonate or polygalacturonate carrier conjugate prepared according to the method of claim 6.

19. An immunogenic modified plant, fruit or synthetic oligogalacmronate or polygalacturonate carrier conjugate prepared according to the method of claim 18 wherein the carrier is tetanus toxoid.

20. An immunogenic modified plant, fruit or synthetic oligogalacmmnate or polygalacturonate carrier conjugate prepared according to the method of claim 9 wherein the pectin is at least 50% O-acetylated.

21. An immunogenic modified plant, fruit or synthetic oligogalacturonate or polygalacturonate carrier conjugate prepared according to the method of claim 9 wherein the pectin is at least 80% O-acetylated.

22. An immunogenic modified plant, fruit or synthetic oligogalacmronate or polygalacturonate carrier conjugate prepared according to the method of claim 9 wherein the pectin is about 160% to about 190% O-acetylated.

23. An immunogenic modified plant, fruit or synthetic oligogalacturonate or polygalacturonate carrier conjugate prepared according to the method of claim 13 wherein the crosslinking agent is cystamine.

24. A pharmaceutical composition comprising the conjugate of claim 17 and a pharmaceutically acceptable diluent.

25. A chemically modified saccharide-carrier conjugate comprising a plant, fruit or synthetic saccharide chemically modified by O-acetylation covalently linked to a carrier, said conjugate elicits antibodies which are immunoreactive with *Salmonella typhi*, Vi capsular polysaccharide of *Salmonella typhi*, and the modified saccharide.

26. The modified plant, fruit or synthetic saccharide-carrier conjugate of claim 25 wherein the saccharide is selected from the group consisting of pectin, D-galacturonan, oligogalacturonate, polygalacturonate, and mixtures thereof.

27. The modified plant, fruit or synthetic saccharide-carrier conjugate of claim 25 wherein the saccharide is pectin.

28. The modified plant, fruit or synthetic saccharide-carrier conjugates of claim 25 wherein the saccharide is at least 50% O-acetylated.

29. The modified plant, fruit or synthetic saccharide-carrier conjugate of claim 25 wherein the saccharide is at least 80% O-acetylated.

30. The modified plant, fruit or synthetic saccharide-carrier conjugate of claim 25 wherein the saccharide is about 160% to about 190% O-acetylated.

31. The modified, plant, fruit or synthetic saccharide carrier conjugate of claim 25 wherein a position on a saccharide subunit selected from the group consisting of $C_2$, $C_3$, and both $C_2$ and $C_3$ is O-acetylated.

32. The modified plant, fruit or synthetic saccharide-carrier conjugate of claim 25 wherein the modified saccharide has a molar ratio of O-acetyl groups: mole galacturonate of at least 0.5:1.

33. The modified plant, fruit or synthetic saccharide-carrier conjugate of claim 25 wherein the modified saccharide has a molar ratio of O-acetyl groups: mole galacturonate of at least 1.6:1.

34. The modified plant, fruit or synthetic saccharide-carrier conjugate of claim 27 wherein the modified saccharide has a molar ratio of O-acetyl groups per mole galacturonate of between about 1.6 to about 1.9 moles of O-acetyl per mole of galacturonate.

35. The modified plant, fruit or synthetic saccharide-carrier conjugate of claim 25 wherein the carrier is selected from the group consisting of bacterial protein, viral protein, tetanus toxoid, diphtheria toxin, *Pseudomonas aeruginosa* exotoxin, *Pseudomonas aeruginosa* toxoid, pertussis toxin, pertussis toxoid, *Clostridium perfringens* exotoxin, *Clostridium perfringens* toxoid, hepatitis B surface antigen, hepatitis B core antigen and Pseudomonas exoprotein A.

36. The modified plant, fruit or synthetic saccharide-carrier conjugate of claim 34 wherein the carrier is tetanus toxoid.

37. The modified plant, fruit or synthetic saccharide-carrier conjugate of claim 25 wherein the saccharide is linked to the carrier by a homobifunctional or heterobifunctional cross-linking agent.

38. The modified plant, fruit or synthetic saccharide-carrier conjugate of claim 37 wherein the crosslinking agent is selected from the group consisting of adipic dihydrazide, ethylene diamine, cystamine, N-succinimidyl-3-(2-pyridyldithio) propionate, N-succinimidyl N-(2-iodoacetyl) -b-alaninate-propionate, succinimidyl 4-(N-Maleimido-methyl) cyclohexane-1-carboxylate, and 3,3'-dithiodipropionic acid.

39. An immunogen against *Salmonella typhi* comprising: a plant, fruit or synthetic saccharide modified by O-acetylation covalently linked to a carrier, said modified saccharide-carrier conjugate elicits antibodies in mammals, said antibodies are specifically immunoreactive against Vi of *Salmonella typhi*.

40. The immunogen of claim 39 wherein the modified plant, fruit or synthetic saccharide has immunological identity with the Vi of *Salmonella typhi* as measured by immunodiffusion.

41. The immunogen of claim 39 wherein the plant or fruit saccharide is derived from a plant or fruit selected from the group consisting of citrus fruit, apples, and beets.

42. The immunogen of claim 39 wherein the saccharide is pectin.

43. The immunogen of claim 39 wherein the saccharide is selected from the group consisting of D-galacturonan, oligogalacturonate, polygalacturonate, and mixtures thereof.

44. The immunogen of claim 39 wherein the carrier is selected from the group consisting of bacterial protein, viral protein, tetanus toxoid, diphtheria toxin, *Pseudomonas aeruginosa* exotoxin, *Ps. aeruginosa* toxoid, pertussis toxin, pertussis toxoid, *Clostridium perfringens* exotoxin, *Clostridium perfringens* toxoid, hepatitis B surface antigen, hepatitis B core antigen and Pseudomonas exoprotein A.

45. The immunogen of claim 39 wherein the saccharide is at least 50% O-acetylated.

46. The immunogen of claim 39 wherein the pectin is at least 80% O-acetylated.

47. The immunogen of claim 39 wherein the carrier is tetanus toxoid.

48. A vaccine against typhoid fever comprising the immunogen of claim 39 and a pharmaceutically acceptable diluent.

49. A method of actively immunizing a human against typhoid fever comprising: administering in vivo a sufficient amount of an O-acetylated plant, fruit or synthetic saccharide linked to a carrier, said amount is sufficient to elicit antibody that binds to Vi of *Salmonella typhi*.

* * * * *

UNITED STATES PATENT AND TRADEMARK OFFICE

CERTIFICATE OF CORRECTION

PATENT NO. : 5,738,855 
DATED : April 14, 1998
INVENTOR(S) : Szu et al.

It is certified that error appears in the above-identified patent and that said Letters Patent is hereby corrected as shown below:

Column 2,
Line 35, a period -- . -- should be added after “spectroscopy”.
Line 38, “Na2SO4” should be -- $Na_2SO_4$ --.

Line 50, “(◇–◇)” should be --(◇–◇)--.

Line 52, “♦–♦)” should be --(⬢–⬢)--

Column 3,
Line 5, “as an effective” should be -- as effective --.
Line 56, “provides method” should be -- provides a method --.

Column 6,
Line 8, “carbodiimide” should be -- carbodimide --.
Line 16, “exclusive” should be -- exclusively --.
Line 23, “repeat” should be -- repeating --.
Line 34, “included” should be -- include --.
Line 38, “exotoxins/toxoid” should be -- exotoxin/toxoid --.
Line 39, “Example” should be -- Examples --.
Line 40, “to are” should be -- to --.
Line 53, “of carboxyl” should be -- of a carboxyl --.
Line 57, “art. (24)” should be -- art (24) --.

Column 7,
Line 1, “are a homobifunctional” should be -- are homobifunctional --.
Line 15, “conjugate” should be -- conjugates --.

Column 8,
Line 28, “form is” should be -- forms are --.
Lines 63-64, “antibody” should be -- antibodies --.

Column 10,
Line 41, “[20]and” should be -- [20] and --.

Column 12,
Line 14, “$^{b\,13}$C N.M.R.” should be -- $^{13}$C N.M.R. --.
Line 28, “1.32x10” should be -- $1.32x10^3$ --.
Line 43, “2.6 mg/mLAb” should be -- 2.6 mg/mL Ab --.
Line 57, “month” should be -- months --.

UNITED STATES PATENT AND TRADEMARK OFFICE

CERTIFICATE OF CORRECTION

PATENT NO. : 5,738,855
DATED : April 14, 1998
INVENTOR(S) : Szu et al.

It is certified that error appears in the above-identified patent and that said Letters Patent is hereby corrected as shown below:

Column 13,
Line 36, "Na $N_3$" should be -- $NaN_3$ --.

Column 14,
Line 34, "$OAcPecTT_2$" should be -- $OAcPec\text{-}TT_2$ --.

Column 15,
Line 53, a period -- . -- should be added after "polysaccharide".

Column 16,
Line 39, a period -- . -- should be added after "146:4308-4314".
Line 45, "(Vi antigert)" should be -- (Vi antigen) --.
Line 46, a period -- . -- should be added after "47:436-499".

Signed and Sealed this

Twenty-ninth Day of June, 2004

JON W. DUDAS
*Acting Director of the United States Patent and Trademark Office*